United States Patent [19]

Stupar et al.

[11] 4,354,660
[45] Oct. 19, 1982

[54] IN-LINE FLOW CONTROL CLAMP

[75] Inventors: James A. Stupar, Waukegan; Stephen D. Smith, McHenry, both of Ill.

[73] Assignee: Baxter Travenol Laboratories Inc., Deerfield, Ill.

[21] Appl. No.: 230,194

[22] Filed: Feb. 2, 1981

[51] Int. Cl.³ .............................................. F16L 55/14
[52] U.S. Cl. ......................................... 251/4; 251/342
[58] Field of Search ..................... 251/4, 9, 331, 342

[56] References Cited

U.S. PATENT DOCUMENTS

| | | | |
|---|---|---|---|
| 314,487 | 3/1885 | Stansbury . | |
| 450,266 | 4/1891 | Truax . | |
| 541,865 | 7/1895 | Lundholm . | |
| 682,172 | 9/1901 | Chaddock . | |
| 854,618 | 5/1907 | Alexander . | |
| 1,186,595 | 6/1916 | Moen . | |
| 1,250,985 | 12/1917 | Day . | |
| 1,789,013 | 1/1931 | McBrien . | |
| 2,127,257 | 8/1938 | Hornberger | 251/5 |
| 2,215,725 | 9/1940 | Martinson | 27/23 |
| 2,540,364 | 2/1951 | Adams | 251/4 |
| 2,614,788 | 5/1946 | Woodward | 251/5 |
| 2,689,564 | 9/1954 | Adams et al. | 251/4 |
| 2,747,935 | 5/1956 | Szantay | 299/104 |
| 3,126,005 | 3/1964 | Smialowski | 128/325 |
| 3,142,472 | 7/1964 | Lipschutz et al. | 251/10 |
| 3,166,819 | 1/1965 | Robbins | 27/21 |
| 3,190,497 | 6/1965 | Anthon | 251/4 |
| 3,305,144 | 2/1967 | Beres et al. | 222/402.13 |
| 3,329,389 | 7/1967 | Clark | 251/4 |
| 3,395,838 | 8/1968 | Beres et al. | 251/4 |
| 3,438,575 | 4/1969 | Rohling | 239/1 |
| 3,509,882 | 5/1970 | Blake | 128/325 |
| 3,579,751 | 5/1971 | Jonckheere | 24/252 |
| 3,598,125 | 8/1971 | Cogley | 128/346 |
| 3,598,288 | 8/1971 | Posgate | 222/70 |
| 3,616,497 | 11/1971 | Esposito, Jr. | 24/81 HS |
| 3,827,438 | 8/1974 | Kees, Jr. | 128/346 |
| 3,863,358 | 2/1975 | Phares, Sr. | 33/367 |
| 3,868,957 | 3/1975 | Doddington | 128/346 |
| 3,996,937 | 12/1976 | Williams | 128/325 |
| 4,024,868 | 5/1977 | Williams | 128/325 |
| 4,063,706 | 12/1977 | Osborne, Sr. | 251/4 |
| 4,070,004 | 1/1978 | Friswell | 251/331 |
| 4,080,989 | 3/1978 | Chapelsky et al. | 137/588 |
| 4,106,508 | 8/1978 | Berlin | 128/346 |
| 4,148,155 | 4/1979 | Allen | 47/59 |
| 4,165,747 | 8/1979 | Bermant | 128/334 |
| 4,192,315 | 3/1980 | Hilzinger et al. | 128/346 |

FOREIGN PATENT DOCUMENTS 790426 2/1958 United Kingdom ............... 251/331

Primary Examiner—H. Jay Spiegel
Attorney, Agent, or Firm—Paul C. Flattery; John A. Caruso; Garrettson Ellis

[57] ABSTRACT

A fluid flow control clamp for in-line insertion on flexible fluid tubing is disclosed. A flow-directing member (10) is positioned intermediate a source of sterilized water or other fluid and a medical humidifier. A blocking element (20) is provided within the flow directing member (10) and inlet and outlet ports (12, 14) are provided on either side of blocking member (20). Resilient tubing (16) is attached to inlet, outlet ports (12, 14) of an appropriate length such that it kinks or crimps (18) when relaxed and unactivated, preventing fluid flow through the clamp.

The clamp is activated by insertion of fingers (24) or other opening means within the loop of resilient tubing (16), unkinking the tubing (16), and permitting fluid flow through the clamp. Release of the resilient tubing (16) causes it to resume its normal kinked position, thereby cutting off the fluid flow through the clamp.

A secondary embodiment discloses a spike connector (30) affixed to the flow-directing member (10) for direct attachment of the clamp to the source of sterilized water. The spike connector (30) may be sheathed with a plastic sleeve (32) to protect it from touch contamination.

7 Claims, 6 Drawing Figures

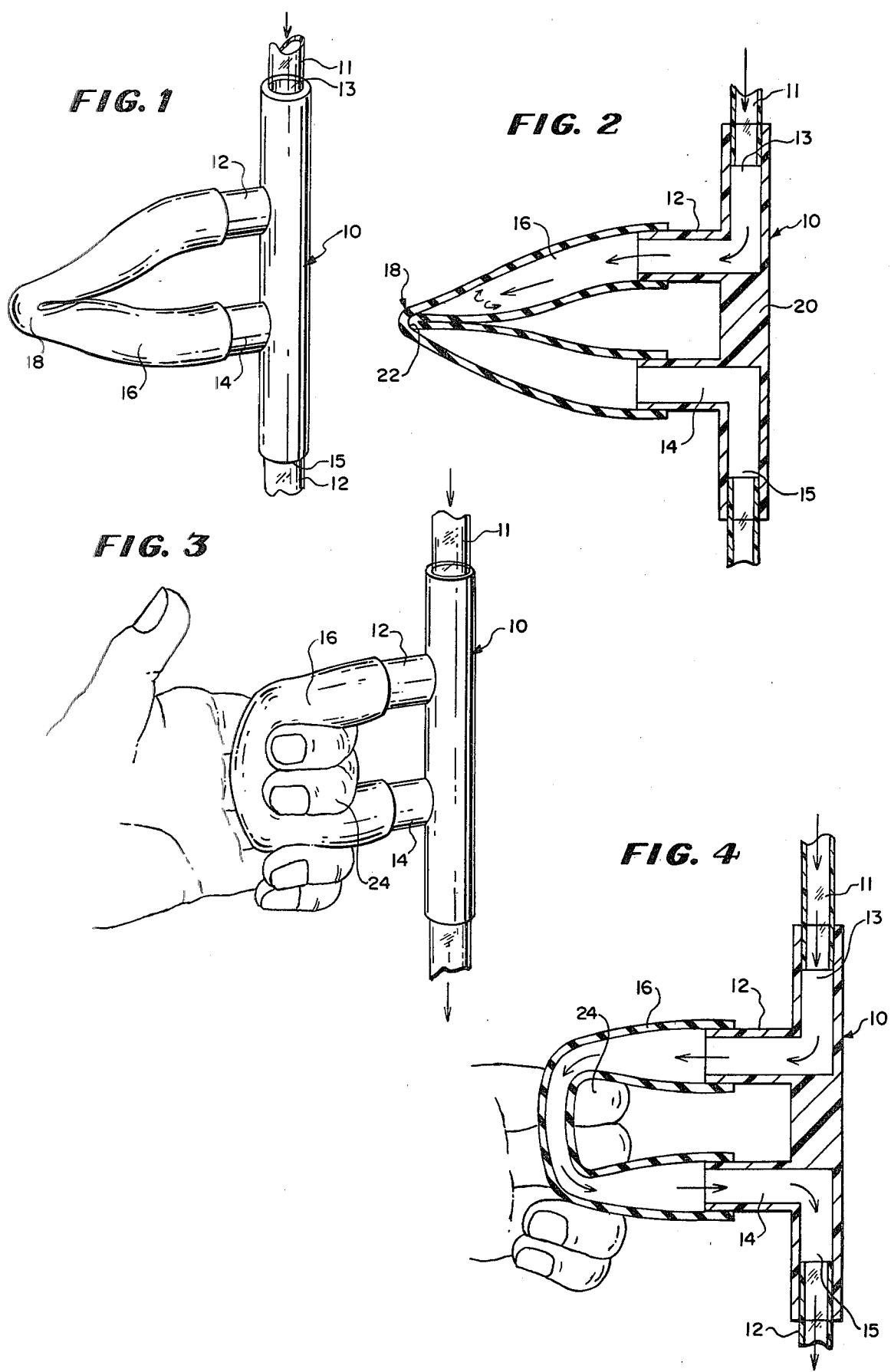

IN-LINE FLOW CONTROL CLAMP

BACKGROUND OF THE INVENTION

In hospital equipment and practice there exists a need for a device which can regulate the flow of fluid supplied to a life-sustaining apparatus or mechanism. A means for clamping off or stopping the fluid supply flow to the apparatus while maintaining the sterile integrity of the system is a necessary requirement. Such a device must be simple, easy to operate, sterilizable, and relatively accident or tamper-proof. The invention of the present application for an in-line clamp fulfills these requirements.

In its present usage, the clamp is employed on in-line tubing connected to a source of sterilized water or other fluid and to a medical humidifier. The humidifier, in turn, is connected to the patient to provide humidified air for promoting upper respiratory functioning.

It is very desirable to maintain the entire system as sterile as possible to prevent infection. The constant attaching, detaching, and reattaching of a sterilized water source to the humidifier, however, would contribute to a lack of maintenance of that sterile environment.

It is necessary, therefore, for the source of water to be constantly attached to the humidifier. It is also necessary to provide a means for clamping of the flow of water from its source to the humidifier so that only a required amount can be supplied at a given time. The present invention provides such an effective clamping means.

Previous clamps for providing the same function have been standard, flexible metal, pinch-cock type sealing clamps. They are originally supplied in an "open" position, maintained open by a rigid plastic block placed between the jaws and around the tubing. In use the block is removed and the tubing can be clamped off.

To supply the fluid the operator or nurse must manually squeeze the pinch-cock arms apart and keep the tubing open until the desired amount of water is supplied. Given the necessity for a rather large and strong clamping device, this can be a tedious and sometimes awkward operation. In addition, the operator, seeking to avoid the time-consuming process, will sometimes replace the pinch-cock on the retaining block surrounding the tubing. This results in a failure of an appropriate regulation of the water supply and the possibility of over-filling of the humidifier with water.

The present device seeks to avoid these problems by providing an in-line clamping means which is normally maintained in a closed position by means of a crimped or kinked tubing offset, but in-line with the source of sterilized water. In operation, the operator manually opens the clamp, permitting the water to flow into the humidifier. It is much more difficult, however, for the clamp to be maintained open without the operator's attention.

In addition, the physical difficulties in using the previous pinch-cock clamp are overcome by the relative ease of operation in the present clamp.

Clamping devices involving a kinking of tubing mechanism are known in the art. Examples would include:

| | |
|---|---|
| Beehler | U.S. Pat. No. 470,776 |
| Rose | U.S. Pat. No. 2,002,835 |
| Tinker | U.S. Pat. No. 2,716,013 |
| Smith | U.S. Pat. No. 2,844,351 |
| Beacham et al. | U.S. Pat. No. 2,922,613 |
| Henderson et al. | U.S. Pat. No. 2,995,334 |
| Wahl | U.S. Pat. No. 3,082,794 |
| Nehring | U.S. Pat. No. 3,100,486 |
| Martinez | U.S. Pat. No. 3,103,335 |
| Anthon | U.S. Pat. No. 3,190,497 |
| Beres et al. | U.S. Pat. No. 3,395,838 |
| LeRoy | U.S. Pat. No. 3,604,425 |

Most of these clamping devices while using a kinked or crimped mechanism format for sealing off the fluid flow, also employ an additional device to mantain the crimp in a closed position.

The clamp of the present invention is maintained normally closed without the use of any external device, taking advantage of the natural kinking action of the tube in the clamp caused by the position in which it is affixed to a fluid directing member attached to the supply tubing. This has the obvious advantage over the device-crimped clamps in that it is not susceptible to accidental opening by bumping or malfunction which would permit unwanted fluid flow through the device. There must be in the present instance an affirmative, intentional opening of the clamp by the operator or else it will remain sealed closed.

SUMMARY OF THE INVENTION

An in-line clamp is provided on flexible tubing for sealing the tubing to the flow of fluid. The clamp consists of a rigid plastic tubing member directly in line with the flexible tubing. The rigid plastic, flow-directing member is in communication with the tubing but blocked off in its center to prevent the flow directly through the member.

The tubing leads to a spiked connector for connecting the tubing and the clamp to a source of sterilized water or other fluid. In a preferred embodiment the spiked connector is sheathed with a plastic protective sleeve to protect the spike from touch contamination when it is connected to the sterilized water source.

In a secondary embodiment, the sheathed, spiked connector is affixed directly to the flow-directing portion of the clamp. This permits the direct attachment of the clamp to the source of sterilized water and may be more useful for some operators in opening the clamp and viewing the source of sterilized water simultaneously.

Just before and after the blocked portion, perpendicular outlet members are provided for directing the fluid flow from the flow-directing member through and into a resilient tubing section. The tubing section is also attached to the outlet on the flow-directing member subsequent to the blocked portion. The resilient side tubing is preferably composed of latex rubber.

The inlet and outlet ports are positioned and the length of flexible rubber tubing is such that the rubber tubing is crimped or kinked, preventing the fluid flow through the clamp, when the rubber tubing is in a relaxed or deactivated position.

To activate the clamp and permit the flow of fluid through the system, the operator inserts two fingers within the loop formed by the resilient tubing, and straightens out or releases the kink in the tubing. This opens the resilient tubing and permits flow through the clamp, and therefore through the system, as long as the operator maintains the resilient tubing in the unkinked position. Upon release or removal of the fingers or other objects, the resilient tubing resumes its normally kinked position and the clamp is again sealed off to fluid flow.

It is apparent therefore that the clamp can only be activated by the intentional opening of it by the operator and that no external clamping device is necessary which may accidentally open the clamp.

A more detailed explanation of the invention is provided in the following description and claims, and is illustrated in the accompanying drawings.

BRIEF DESCRIPTION OF THE DRAWINGS

FIG. 1 is a perspective view of the clamp in the normal, unactivated, closed position.

FIG. 2 is a profiled, sectional view of the clamp in the unactivated or closed position.

FIG. 3 is a perspective view in the open or activated position illustrating a manual means for opening.

FIG. 4 is a sectional, profiled view of the clamp in the open or activated position.

DETAILED DESCRIPTION OF THE PREFERRED EMBODIMENT

Figure 5:
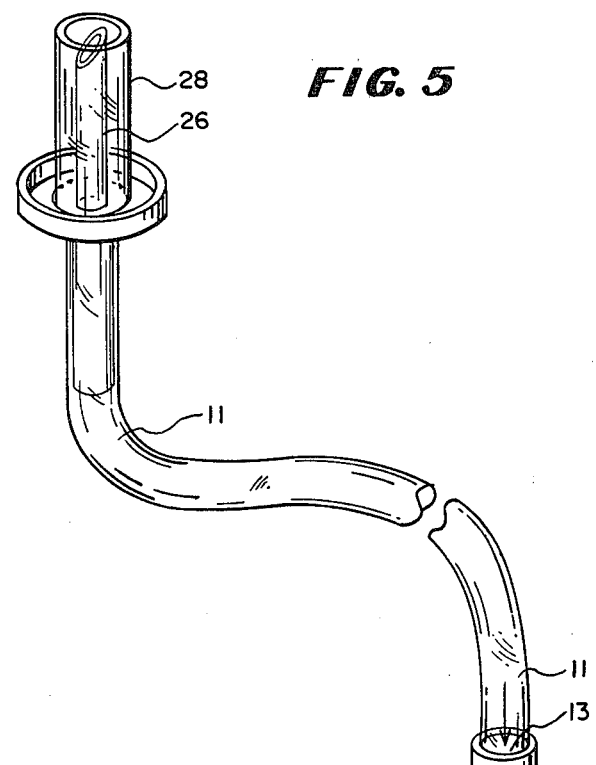
FIG. 5 is a perspective view of the clamp showing the sheathed spike connector on the flexible tubing.

Referring to FIG. 1, a perspective view of the flow control clamp is shown comprising a flow directing member (10) positioned in-line with flexible tubing (11). The clamp defines openings (13, 15) for fluid flow, respectively leading from a source of sterilized water or other fluid (not shown), and into the intended point of delivery (not shown); in the present case a hospital humidifier. An outlet port (12) and inlet port (14) are positioned leading from and to the flow directing member (10) in a position perpendicular to the fluid flow. Connected to the inlet and outlet ports (12, 14) is a length of resilient tubing (16) attached to inlet, outlet ports (12, 14) by conventional friction means.

The inlet, outlet ports (12, 14) are positioned a distance apart on the flow directing member (10) and the length of resilient tubing (16) is such that a crimped area (18) forms within the resilient tubing (16). It is this crimp or kink (18) which is maintained in the resilient tubing (16) by virtue of the length of the tubing (16) and its positioning, that causes the sealing off of the clamp to the flow of fluids.

In FIG. 2, a sectional view of the clamp, an internal block (20) within the flow directing member (10) is shown which routes the fluid flow out outlet port (12), through the resilient side tubing (16) and back into the flow-directing member (10) through inlet (14). Also shown is the internal crimp seal (22), of crimp (18) which seals off the clamp in its normal, unactivated configuration.

The resilient tubing (16) is composed of a material which is capable of being uncrimped when activated and returning to its normally closed crimped position upon release. In the preferred embodiment of the present invention, the resilient tubing (16) is composed of latex rubber.

In an additional feature of the preferred embodiment, as shown in FIG. 5, the flexible tubing (11) leads to a spiked connctor (26) which is inserted through the opening port (not shown) of the source of sterilized water. The spiked connector (26) may be surrounded by a protective plastic sheath (28). The protective sheath acts to prevent touch contamination of the system when the spike connector (26) is being inserted into the water source.

Figure 6:
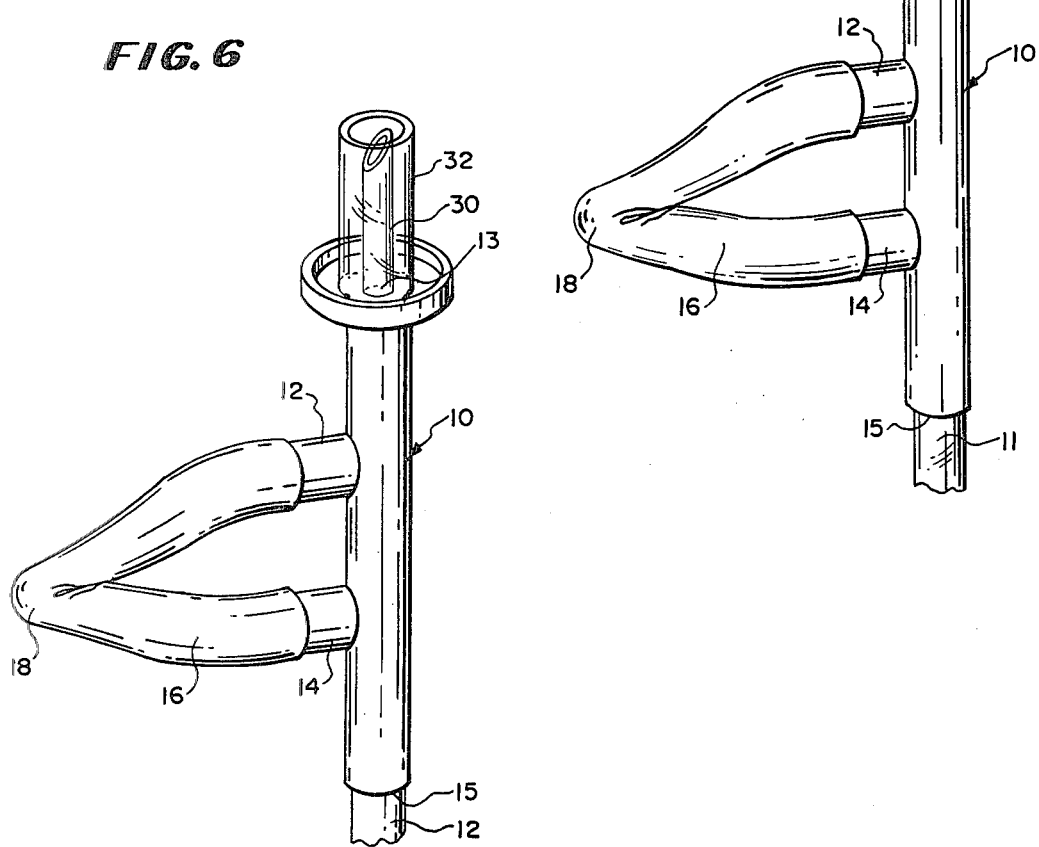
FIG. 6 is a perspective view of the clamp showing the sheathed spike connector directly attached to the clamp.

In a secondary embodiment, as shown in FIG. 6, a spiked connector (30) may be directly affixed to the first opening (13), without using flexible tubing (11). The spiked connector (30) may be surrounded by a protective plastic sheath (32), as described above in the preferred embodiment.

Having the spiked connector (30) directly connected to the clamp allows the clamp to be inserted directly into the sterile water source and may be particularly useful in simultaneously monitoring the flow of sterile water from the source while operating the clamp. It may also provide a more stationary fixation of the clamp during operation than the clamp attached to the mobile flexible tubing (11) and may be an aid in operation.

In operation, as illustrated in FIG. 3, the operator inserts two or more fingers (24) within the loop formed by resilient tubing (16) and the inlet, outlet ports (12, 14) and manually unkinks the crimp (18), thereby opening the resilient tubing (16) and the clamp to fluid flow.

The internal operation during activation is shown in FIG. 4 in a profile sectional view of the device. Once activated by fingers (24) or other suitable device, fluid flow is permitted through flexible tubing (11), into flow directing member (10), out through outlet port (12), through resilient tubing (16) back into the device through inlet port (14), and continuing on again through flexible tubing (11).

When the desired amount of fluid has passed through the clamping device, the operator simply removes his or her fingers (24) and the resilient tubing (16) resumes its normal crimped position, thereby sealing the clamp again to fluid flow. The device is simple to operate, easily manufactured and, because it has no external clamping means to keep the crimp in place, it is unsusceptible to accidental opening or malfunction.

Although an illustrative embodiment of the invention has been shown and described, it is understood that various modifications and substitutions may be made without departing from the novel spirit and scope of the present invention.

What is claimed is:
1. A clamp comprising:
   a flow directing member, portions of said member defining a first opening through which a fluid can be delivered into the clamp and a second opening out of which the fluid can be directed from the clamp, said openings being axially aligned;
   inlet and outlet means in said flow-directing member;
   means within said flow-directing member for internally blocking the flow of fluid directly and axially between said openings;
   resilient sealing means connected to said inlet and outlet means in bypassing relation around said internally blocking means; and
   a crimped area within said resilient sealing means which prevents fluid flow through said sealing means, said crimped area spontaneously springing shut to a closed crimped state unless manually uncrimped, and said crimped area being capable of being uncrimped, to permit fluid flow through said clamp.

2. A clamp as claimed in claim 1 in which said resilient sealing means includes resilient tubing of an appropriate length such that such tubing, when connected to said inlet and outlet means, kinks to form said crimped area, is capable of being uncrimped by manual manipulation, and returns to its crimped orientation upon elimination of such manual manipulation.

3. A clamp device as claimed in claim 2 in which said resilient sealing means is made of latex rubber.

4. A clamp as claimed in claims 1 or 2 in which said first opening is connected to a spiked connecting means, the spike portion of said spiked connecting means being surrounded by protective sheathing means for protecting said spike from touch contamination.

5. A clamp as claimed in claim 4 in which flexible tubing for fluid delivery is attached between said spiked connecting means and said first opening.

6. In a clamp including a flow directing member, portions of said member defining a first opening through which a fluid can be delivered into the clamp and a second opening out of which fluid can be directed from the clamp, said openings being axially aligned;

inlet and outlet means in said flow-directing member;

means within said flow-directing member for internally blocking the flow of fluid directly and axially between said openings;

resilient sealing means connected to said inlet and outlet means in bypassing relation around said internally blocking means; and a crimped area within said resilient sealing means which prevents fluid flow through said sealing means, said crimped area spontaneously springing shut to a closed crimped state unless manually uncrimped, and said crimped area being capable of being uncrimped, to permit fluid flow through said clamp, the method of operating said clamp comprising the steps of:

placing a clamp in communication with a fluid flow line;

uncrimping the crimped, resilient tubular means;

directing fluid flow from the fluid line into the first opening in the flow-directing member of the clamp; and, directing the fluid flow through the inlet means and the uncrimped tubular resilient means, through the outlet means and the second opening back into the fluid line.

7. The method of claim 6 wherein uncrimping the crimped, resilient means is accomplished by the manipulation of a person's fingers.

* * * * *